(12) United States Patent
Takeuchi et al.

(10) Patent No.: US 6,177,513 B1
(45) Date of Patent: Jan. 23, 2001

(54) METHOD FOR EVALUATING ARTIFICIAL RECEPTORS (75) Inventors: Toshifumi Takeuchi; Jun Matsui; Daigo Fukuma, all of Hiroshima; Toshihiro Mizukami, Kobe, all of (JP)

(73) Assignees: Toshifumi Takeuchi, Hiroshima; Sysmex Corporation, Hyogo, both of (JP)

(*) Notice: Under 35 U.S.C. 154(b), the term of this patent shall be extended for 0 days.

(21) Appl. No.: 09/266,942

(22) Filed: Mar. 12, 1999

(30) Foreign Application Priority Data

Aug. 28, 1998 (JP) .................................................. 10-243634

(51) Int. Cl.[7] .......................... B01D 15/00; B01J 39/00; C02F 1/42; C08J 9/00
(52) U.S. Cl. ......................... 525/54.1; 521/99; 210/660; 210/661; 210/663; 252/408.1; 436/8; 436/163
(58) Field of Search .............................. 521/99; 525/54.1; 210/660, 661, 663; 252/408.1; 436/163, 8

(56) References Cited

FOREIGN PATENT DOCUMENTS

| 8-15160 | 1/1996 | (JP) . |
| 8-50632 | 7/1996 | (JP) . |

OTHER PUBLICATIONS

Gunter Wulff, "Molecular Imprinting in Cross–Linked Materials with the Aid of Molecular Templates", pp. 1812–1832; Angew. Chem. Int Ed. Engl., 34 (1995).
Jun Matsui et al., Analytical Chemistry, 67 (1995), "A Molecularly Imprinted Synthetic Polymer Receptor Selective for Atrazine", pp. 4404–4408.
Jun Matsui et al., Chemistry Letters, (1995), "Atrazine–selective Polymer Prepared by Molecular Imprinting Technique", p. 489.
Jun Matsui et al., Analytical Chemistry, 65 (1993), "Molecular Recognition in Continuous Polymer Rods Prepared by a Molecular Imprinting Technique", pp. 2223–2224.

*Primary Examiner*—Nathan M. Nutter
(74) *Attorney, Agent, or Firm*—Birch, Stewart, Kolasch & Birch, LLP

(57) ABSTRACT

A method for evaluating an artificial receptor includes subjecting a functional monomer and a crosslinker in the presence of a template substance in a vessel into polymerization, thereby forming a resultant polymer with the template substance usually in the form of a thin film, dissociating the template substance from the polymer and removing it from the vessel by washing an inside of the vessel, thereby to prepare an artificial receptor, feeding a solution of the same or different template substance into the vessel to associate the template substance with the resulting polymer; then determining the amount of the template substance remaining in the vessel, and evaluating the artificial receptor on the basis of a determination result.

18 Claims, 6 Drawing Sheets

Calibration curve

METHOD FOR EVALUATING ARTIFICIAL RECEPTORS

CROSS-REFERENCE TO RELATED APPLICATION

This application is related to Japanese application No.10 (1998)-243634 filed on Aug. 28, 1998, whose priority is claimed under 35 USC § 119, the disclosure of which is incorporated by reference in its entirety.

BACKGROUND OF THE INVENTION

1. Field of the Invention

The present invention relates to a method for evaluating artificial receptors, more particularly an evaluation method for use in development of artificial receptors, which have been recently growing in use as separating agents for chemicals, sensor materials for chemicals, reagents for immunoassays and the like.

2. Description of Related Art

In living bodies, a variety of functions are expressed by proper recognition of a huge amount of chemical substances. For example, an enzyme effectively catalyzes a chemical reaction in a living body by recognizing a specific substance. Also various kinds of receptors existing in cell membranes bind selectively to specific substances and transfer extracellular information received from the specific substances into cells. The cells in turn exercise functions required in a living body such as suppression, regulation and the like on the basis of the extracellular information.

Artificial receptors are those artificially designed and synthesized to imitate such receptors and exhibit good molecular recognition functions. For designing and synthesizing such artificial receptors, there are proposed several methods, among which "Molecular Imprinting method by Wuff, G., Angew.Chem.,Int.Ed.Engl.,34,1812–1832(1995) is said to be particularly excellent and preferable.

According to the Molecular Imprinting method (hereinafter referred to as MI method), an artificial polymeric receptor can be prepared by polymerizing a polymerizable organic compound (a functional monomer) which interacts with a template substance (also referred to as a key molecule, imprint molecule or template molecule) and a crosslinker(i.e., crosslinking monomer) in the presence of the template substance and then releasing and removing the template substance from the resultant polymer. This polymeric receptor is a polymer characterized by having a cavity fit to the molecular morphology and size of the template substance. In addition to that, the polymer obtained by the MI method (hereinafter referred to as a molecularly imprinted polymer) is physically and chemically stable and has an excellent storage endurance.

Published Japanese Patent Application No. HEI 8(1996)-506320 (corresponding to the International Patent Application Publication No. WO94/11403) discloses the use of a molecularly imprinted polymer (artificial antibody) for detecting an antigen in immunoassay.

Further, Japanese Unexamined Patent Publication No. HEI 8(1996)-15160 discloses a biomimetic sensor using a thin molecularly imprinted polymer.

With a view to obtaining a suitable molecularly imprinted polymer, however, the MI method has several problems. First, it is necessary to study suitable polymerization conditions about combination and proportion of components, i.e., the functional monomer and crosslinker, with respect to the template substance as well as a solvent to be used for polymerization. Moreover, in order to evaluate the obtained molecularly imprinted polymer, the polymer must be crushed into pieces, packed in a column and evaluated about to what extent the polymer can recognize the template substance. This whole evaluation process consumes considerable time and labor.

A conventional in situ method by J. Matsui, T. Kato, T. Takeuchi, M. Suzuki, K. Yokoyama, E. Tamiya, and I. Karube, Anal.Chem., 65, 2223(1993), which was developed for reducing such time and labor, discloses a method for preparing a molecularly imprinted polymer directly in a column for HPLC by feeding a mixture of a template substance, functional monomer(s), a crosslinker, a solvent, an initiator for polymerization and the like in the column and polymerizing in situ. According to this method, the ability of the molecularly imprinted polymer to recognize the template molecule can be evaluated only by connecting the resulting column to a pump for HPLC and subjecting to HPLC analysis. However, this method is not a satisfactory one because it still needs much time and work.

SUMMARY OF THE INVENTION

The present inventors have found a new in situ method for evaluating an artificial receptor. Accordingly, the present invention provides a method for evaluating an artificial receptor, which includes subjecting a functional monomer and a crosslinker in the presence of a template substance(i.e., a substance to be recognized) in a vessel into polymerization, thereby forming a resultant polymer with the template substance usually in the form of a thin film; dissociating the template substance from the polymer and removing it from the vessel by washing the inside of the vessel, thereby to prepare an artificial receptor; feeding a solution of the same or different template substance into the vessel to associate the template substance with the artificial receptor; and then measuring an amount of the template substance remaining in the vessel and evaluating the artificial receptor on the basis of a determination result.

In another aspect, the present invention provides an artificial receptor obtained by the above-mentioned method of the invention.

In a further aspect, it provides a method for quantitating a template substance comprising the steps of: subjecting a functional monomer and a crosslinker in the presence of a template substance in a vessel into polymerization, thereby forming a resultant polymer with the template substance usually in the form of a thin film; dissociating the template substance from the polymer and removing it from the vessel by washing an inside of the vessel, thereby to prepare an artificial receptor; feeding a sample of a template substance, which may be the same or different with the above template substance, in an unknown concentration into the vessel to associate the template substance with the artificial receptor, separating the associated product; and measuring an optical parameter of the template substance in the artificial receptor.

DESCRIPTION OF THE PREFERRED EMBODIMENTS

According to the method for evaluating an artificial receptor of the present invention, a functional monomer and a crosslinker in the presence of a template substance, further optionally in the presence of a solvent and an initiator for polymerization, are subjected into polymerization in a vessel, thereby forming a resultant polymer with the template substance usually in the form of a thin film. Then the template substance is dissociated from the polymer and removed from the vessel by washing the inside of the vessel, whereby an artificial receptor is prepared. A solution of a template substance which may be the same or different with the above template substance is poured into the vessel in order to associate the template substance with the artificial receptor. Then an amount of the template substance remaining in the vessel is determined, and on the basis of a determination result, the artificial receptor is evaluated on affinity and selectivity to the template substance.

The template substance in the present invention means a substance to be recognized by an artificial receptor, and is not particularly limited to a specific kind of substance. However, several examples thereof are drugs (e.g., cinchonine, cinchonidine, theophylline, diazepam, morphine and ephedrine), hormones (e.g., cortisol and enkephalin), pesticides (e.g., atrazine and ametryn), proteins (e.g., RNase A and urease), amino acids (e.g., phenylalanine, tryptophan, tyrosine and aspartic acid), carbohydrates (e.g., galactose, glucose and fucose), co-enzymes (e.g., pyridoxal) and nucleotide bases (e.g., adenine).

Examples of the functional monomer used in the present invention are vinyl monomers such as carboxylic acids (e.g., acrylic acid, methacrylic acid, itaconic acid, trifluoromethacrylic acid, 2-(trifluoromethyl)acrylic acid, vinylbenzoic acid and 4-vinylbenzyliminodiacetic acid), sulfonic acids (e.g., 2-acrylamido-2-methyl-1-propane sulfonic acid), and heteroaromatic bases (e.g., vinylpyridine, vinylimidazole and 2,6-bisacrylamidopyridine). These functional monomers may be used singly or as a combination thereof.

Examples of the crosslinker used in the present invention are ethylene glycol, ethylene glycol dimethyl acrylate, 1,4-divinylbenzene, N,N'-methylene-bisacrylamide, N,N'-phenylene-bisacrylamide, ethylene glycol dimethacrylate, trimethylolpropane trimethacrylate, pentaerythritol triacrylate, pentaerythritol tetraacrylate and trimethylpropane trimethacrylate.

An appropriate combination of the functional monomer and the crosslinker can be easily selected by a person skilled in the art, taking the consideration of chemical and physical properties of these materials.

The solvent is desired to select a suitable one taking into consideration that it does not harm the interaction of the functional monomer and the template substance, can solve each material for polymerization and can be a porogen to provide porosity for the polymer. Examples thereof are toluene, dichloromethane, chloroform, acetonitrile and tetrahydrofuran, among which toluene and dichloromethane are preferred.

The amount of the functional monomer to be used may vary depending on the kinds of the template substances and the functional monomers, but may be 1 to 100 moles with respect to one mole of the template substance in usual cases.

The crosslinker may generally be used in an excess amount with respect to that of the functional monomer.

The polymerization may be radical polymerization (e.g., bulk, suspension, solution, emulsion, seed, dispersion, reverse suspension and soap-free polymerization), ion polymerization (e.g., anionic and cationic polymerization), melt polymerization, solid-state polymerization, interfacial polymerization and the like.

For example, a functional monomer, a crosslinker, a template substance, a solvent and a polymerization initiator are put into a vessel and are polymerized with UV irradiation under nitrogen atmosphere at a low temperature.

Alternatively, they can polymerize at an elevated temperature (e.g., at 40 to 70° C., especially at 45° C.) without UV irradiation.

After polymerization, a polymer with the template substance associated thereto is formed usually in the from of a thin film inside of the vessel. The vessel used in the present invention may be a container which can hold polymerization components. The vessel may be of any material, and the shape and the size thereof are not particularly limited. The preferred one is a glass vial.

A washing liquid used for washing the resultant polymer can be selected depending on how the template substance and the polymer associate, but preferably does not solve the polymer itself and can dissociate the template substance from the polymer. The examples of the washing liquid may be an aliphatic alcohol(e.g., methanol, ethanol and propanol), water, an acid(e.g., inorganic acids such as hydrochloric acid and hydrobromic acid and organic acids such as acetic acid), a base(e.g., triethylamine) or a mixture thereof in usual cases.

Figure 1:
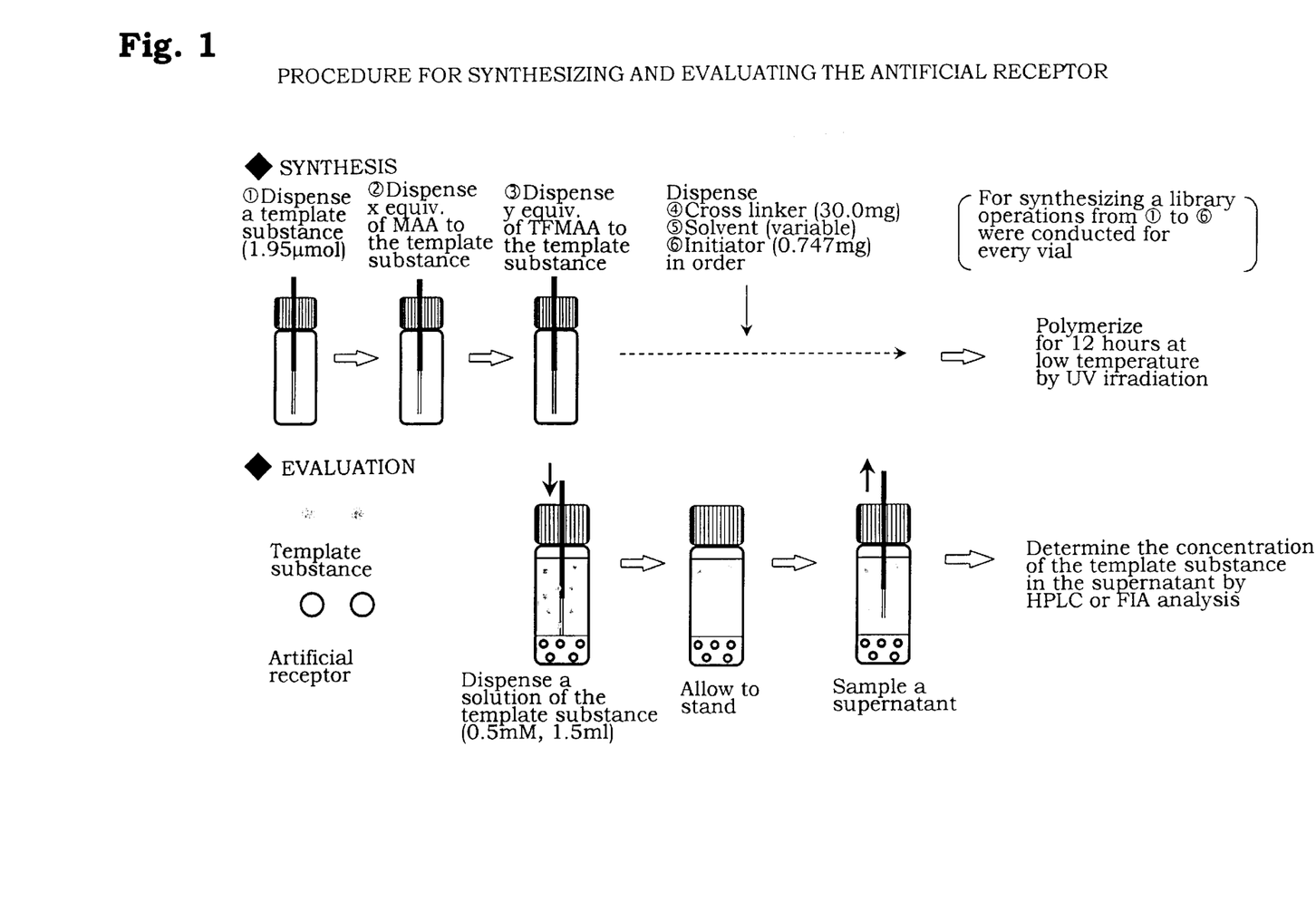
FIG. 1 is a flowchart illustrating a procedure for synthesizing and evaluating an artificial receptor in accordance with the present invention.

One preferred embodiment of the present invention is conducted as shown in FIG. 1. That is, a method for evaluating an artificial receptor according to the present invention comprises dispensing a template substance and a functional monomer in a vessel; dispensing a crosslinker, and optionally a solvent and an initiator for polymerization, in the vessel; subjecting to polymerization to form a resultant polymer with the template substance associated thereto usually in the form of a thin film; dissociating the template substance from the polymer and removing it from the vessel by washing an inside of the vessel, thereby to prepare an artificial receptor; feeding a solution of the same or different template substance into the vessel to associate the template substance with the resulting polymer; then determining an amount of the template substance remaining in the vessel; and evaluating the artificial receptor on the basis of a determination result.

According to the present invention, plural of vessels may be used for preparing a variety of artificial receptors.

Further, according to the present invention, this method for evaluating artificial receptors may be carried out by using a combinatorial chemistry technique. In other words, in the method of the present invention, a variety of the artificial receptors are prepared simultaneously and then evaluated continuously by the combinatorial chemical technique using plural vessels. More particularly, the method of the invention can be efficiently carried out in a substantially automated way by use of a synthesizing robot for combinatorial library, an assay robot for evaluating libraries or the like which robot is adapted to pipet materials for polymer preparation (e.g., one template substance, in the combination with different proportions and kinds of functional monomers and crosslinkers, optionally of the solvent and the initiator for polymerization), to feed and discharge the washing liquid for dissociating the template substance from the obtained polymers, to feed a solution of the same or different template substance into the vessels, to take supernatants out of the vessels, to determine the quantity of the template substance contained in the supernatants and so on.

The quantity of the template substance in the supernatants can be determined by measurement of UV absorption, fluorescence, chemical light emission or biological light emission, by electrochemical detection, or by means of enzymatic activity as indicator, in combination with the HPLC analysis and flow injection analysis.

It is noted that the artificial receptor can be evaluated by the following simplified modification of the method of the invention. That is, the functional monomer and crosslinker in the presence of the template substance are subjected into polymerization in vessels, thereby forming the polymer with the template substance, and then the amount of unassociated template substance in supernatant is measured. The obtained artificial receptor is evaluated on the basis of the measurement results. This simplified method can evaluate the artificial receptor with a certain degree of accuracy.

In another aspect, the present invention provides a method for quantitating a template substance comprising the steps of subjecting a functional monomer and a crosslinker in the presence of a template substance in a vessel into polymerization, thereby forming the resultant polymer with the template substance usually in the form of a thin film; dissociating the template substance from the polymer and removing it from the vessel by washing an inside of the vessel, thereby to prepare an artificial receptor; feeding a sample of a template substance, which may be the same or different with the above template substance, in an unknown concentration into the vessel to associate the template substance with the artificial receptor, separating the associated product; and measuring an optical parameter (absorbance, intensity of fluorescence or oxygen activity) of the template substance in the artificial receptor. For example, a concentration of the sample of the template can be obtained by comparing the obtained optical parameter with optical parameters obtained from authentic samples.

EXAMPLES

The invention is now described in further detail by way of non-limitative examples thereof.

Example 1

(1) Preparation of Polymer Library (PL(Ame))

Polymers selective for ametryn were prepared with reference to known methods by J. Matsui, Y. Miyoshi, O. Doblhoff-Dier, T. Takeuchi, *Analytical Chemistry*, 67,4404–4408(1995) and by J. Matsui, O. Doblhoff-Dier, T. Takeuchi, *Chem. Lett.*, 489(1995)]. Ametryn (i.e., 4-(ethylamino)-6-(isopropylamino)-2-methylthio-1,3,5-triazine) and atrazine (i.e., 2-chloro-4-(ethylamino)-6-(isopropylamino)-1,3,5-triazine) are triazine herbicides.

FIG. 1 is a flowchart illustrating a synthesizing and evaluating process. Polymers for ametryn were prepared according to FIG. 1. Ametryn (1.95 $\mu$mol, produced by Wako Pure Chemical Industries, Japan) was used as a template substance, and methacrylic acid (hereinafter referred to as MAA, produced by Katayama Chemical, Japan) and 2-(trifluoromethyl)acrylic acid (hereinafter referred to as TFMAA, produced by Tokyo Chemical Industry, Japan) were used as functional monomers. Ethylene glycol dimethacrylate (30.0 mg, hereinafter referred to as EGDMA, produced by Katayama Chemical), 2,2'-azobisisobutylonitrle (0.747 mg, hereinafter referred to as AIBN, produced by Wako Pure Chemical Industries) and chloroform (59.0 $\mu$L, produced by Katayama Chemical) were used as a crosslinker, an initiator and a solvent for polymerization, respectively. Here, the amount ratio of the above-mentioned two functional monomers with respect to ametryn was varied in 49 ways with each of the functional monomers used within the range of 0 to 6 equivalents to ametryn. Methylmethacrylate (produced by Wako Pure Chemical Industries) was used in addition to the functional monomers in such an amount that the total amount of the functional monomers and methylmethacrylate was 12 equivalents to ametryn.

These materials were pipetted into each vessel using the synthesizing robot, the atmosphere in the vessels was replaced with nitrogen gas, and the materials in the vessels were allowed to polymerize at 5° C. for 12 hours under UV irradiation. A washing liquid (methanol/water/acetic acid= 7/2/1 by volume) was fed into each vessel and then sucked out therefrom repeatedly 10 times in order to remove ametryn, unreacted functional monomers and crosslinker, and the initiator from the vessel. Then, chloroform was fed into each vessel and sucked therefrom repeatedly three times in order to replace the washing liquid in the vessel with chloroform. As a result, a polymer library of 49 kinds of ametryn-imprinted polymers was obtained. This polymer library is hereinafter referred to as PL(Ame). The polymers were formed to cover the inside surfaces of the vessels.

(2) Binding Test of PL(Ame) and ametryn

Figure 2:
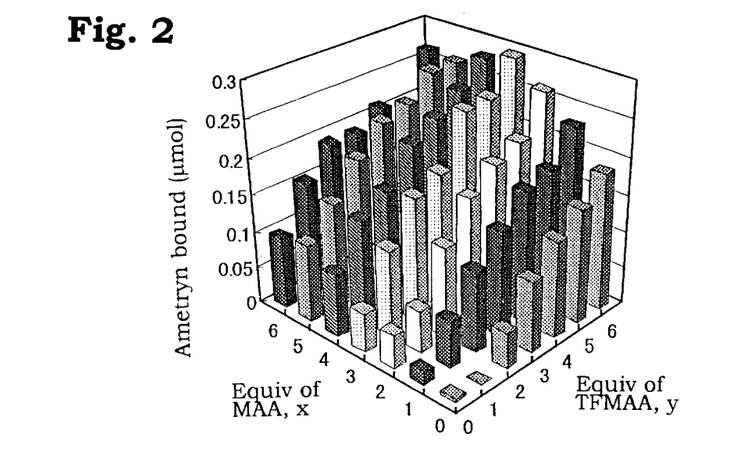
FIG. 2 represents the amounts of ametryn bound to ametryn-imprinted polymers in an ametryn-imprinted polymer library (PL(Ame)) in accordance with the present invention.

In each of the vessels where PL(Ame) was produced, 1.5 ml of a 500 $\mu$M ametryn solution in chloroform was fed. The vessels were allowed to stand for 24 hours. Then, the concentrations of unreacted ametryn in the vessels were determined by the HPLC analysis or flow injection analysis. The amounts of ametryn bound to the polymers of PL(Ame)

were calculated from the difference between the initial ametryn concentration (500 μM) and the ametryn concentration in the supernatants. The results are shown in FIG. 2.

(3) Binding Test of PL(Ame) and atrazine

After the above-mentioned test (2), the washing liquid (methanol/water/acetic acid=7/2/1 by volume) was fed in the vessels and sucked therefrom repeatedly ten times in order to remove ametryn from the vessels. Then chloroform was fed in the vessels and sucked therefrom repeatedly three times in order to replace the washing liquid in the vessels with chloroform.

Figure 3:
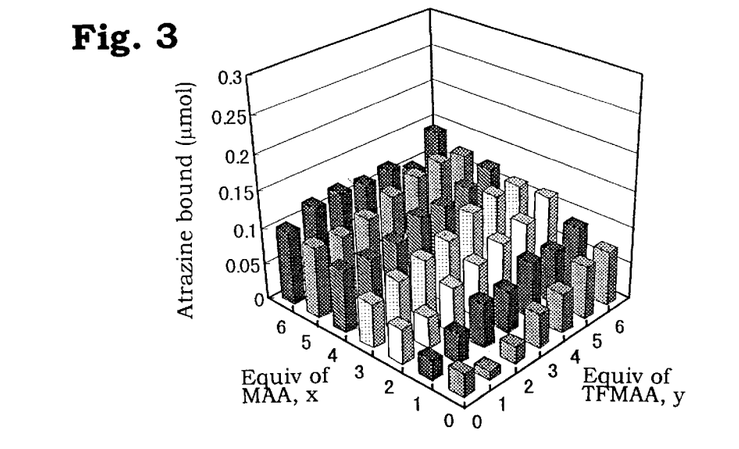
FIG. 3 represents the amounts of atrazine bound to the ametryn-imprinted polymers in the ametryn-imprinted polymer library (PL(Ame)) in accordance with the present invention.

The same procedure as in Example 1(2) was carried out except that a 500 μM atrazine solution in chloroform was fed to PL(Ame), and the amounts of atrazine bound to the polymers of PL(Ame) were calculated. The results are shown in FIG. 3.

For HPLC analysis of ametryn and atrazine in the supernatants, used was a Hitachi HPLC system (Hitachi L-6200 Intelligent Pump, L-3000 photodiode array detector) equipped with a reversed phase column (Supelco LC-8-DB (4.6 mm×150 mm, I.D.)). For injecting the supernatants from the vials to the HPLC system, used was an automatic sampler injector (Gilson, 231XL). In the HPLC analysis, ammonium acetate buffer (pH6.0, 0.1 M)/acetonitrile (6/4 by volume in the case of detecting ametryn and 7/3 by volume in the case of detecting atrazine) was run at a flow rate of 1.0 ml/min. as an eluent, and a UV absorption wavelength of an UV detector was set to 260 nm. For the flow injection analysis, the column was taken away from the above-described system and chloroform was used as a carrier solvent.

(4) Evaluation of PL(Ame) on Selectivity to ametryn

Figure 4:
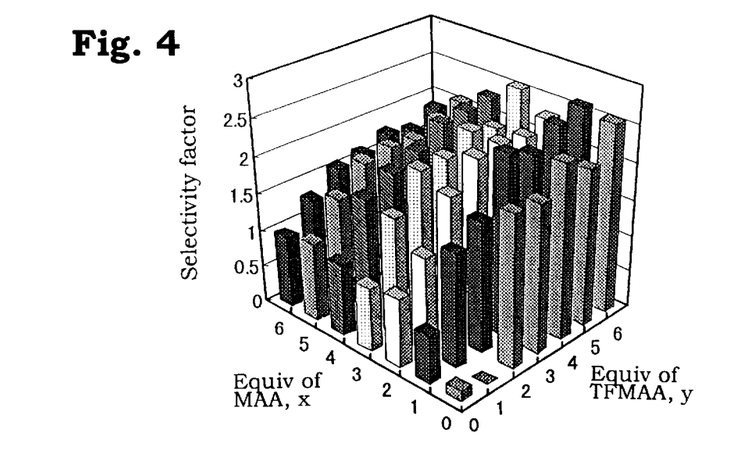
FIG. 4 represents the selectivities of the ametryn-imprinted polymers to ametryn in accordance with the present invention.

The ratios of the amounts of ametryn bound to the polymers in PL(Ame) with respect to the amounts of atrazine bound to the same polymers in PL(Ame) were respectively calculated as the selectivites to ametryn of the ametryn-imprinted polymers belonging to PL(Ame). The results are shown in FIG. 4.

FIG. 2 shows that the amount of ametryn bound to an ametryn-imprinted polymer tends to increase as either of MAA and TFMAA is increased. FIG. 3 shows that the amount of atrazine bound to the ametryn-imprinted polymer does not increase much even if either of MAA and TFMAA is increased. Further, FIG. 4 shows that MAA does not contribute to the selectivity to ametryn of the ametryn-imprinted polymer but that the more TFMAA the polymer contains, the more improved selectivity to ametryn the polymer exhibits. Therefore, it is suggested that TFMAA is a superior functional polymer to MAA with respect to the ametryn selectivity. It is also found that the polymer in which six equivalents of TFMAA are used with respect to ametryn is particularly excellent.

Example 2

(1) Preparation of Polymer Library (PL(Atr))

The same procedure as described in Example 1 (1) was carried out except that atrazine (obtained from a herbicide by purification) was used as the template substrate in order to synthesize a polymer library of 49 kinds of atrazine-imprinted polymers (hereinafter referred to as PL(Atr)).

(2) Binding Test of PL(Atr) and atrazine

Figure 5:
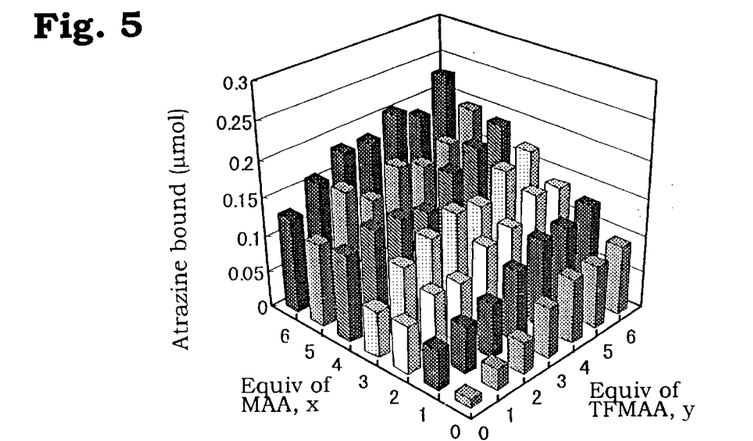
FIG. 5 represents the amounts of atrazine bound to atrazine-imprinted polymers in an atrazine-imprinted polymer library (PL(Atr)) in accordance with the present invention.

The same procedure as described in Example 1(2) was carried out except that a 500 μM atrazine solution in chloroform was fed into each of the vessels where PL(Atr) was produced to calculate the amount of atrazine bound to each of the polymers of PL(Atr). The results are shown in FIG. 5.

(3) Experiment on the Binding of PL(Atr) to ametryn

Figure 6:
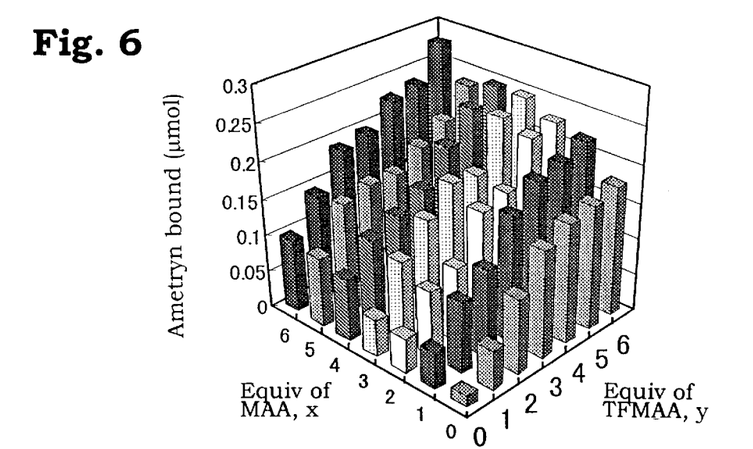
FIG. 6 represents the amounts of ametryn bound to the atrazine-imprinted polymers in the atrazine-imprinted polymer library (PL(Atr)) in accordance with the present invention.

The same procedure as described in Example 1(3) was carried out except that a 500 μM ametryn solution in chloroform was fed into the vessels where PL(Atr) was prepared in order to calculate the amount of ametryn bound to each of the polymers of PL(Atr). The results are shown in FIG. 6.

(4) Evaluation of PL(Atr) on Selectivity to atrazine

Figure 7:
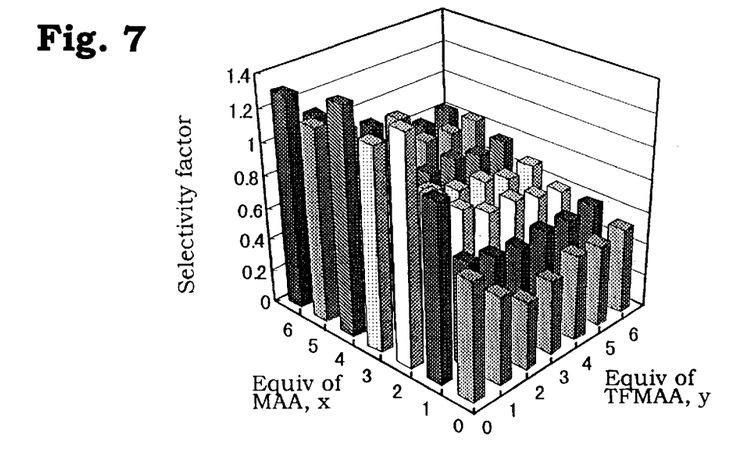
FIG. 7 represents the selectivities of the atrazine-imprinted polymers to atrazine in accordance with the present invention.

The ratios of the amounts of atrazine bound to the atrazine-imprinted polymers in PL(Atr) to the amounts of ametryn bound to the same polymers in PL(Atr) were respectively calculated as the selectivities to atrazine of the atrazine-imprinted polymers belonging to PL(Atr). The results are shown in FIG. 7.

FIG. 5 shows that, in the case of a polymer not containing TFMAA as a functional polymer, i.e., in the case where the amount of TFMAA was zero, the amount of atrazine bound to the atrazine-imprinted polymer increases when the amount ratio of MAA increases with respect to atrazine. It is also found that in the case where the amount of MAA is small, as the amount ratio of TFMAA increases, the amount of atrazine bound to the atrazine-imprinted polymer increases. It is also found from FIG. 7 that the smaller amount ratio of TFMAA the atrazine-imprinted polymer has with respect to atrazine, the more improved selectivity to atrazine the atrazine-imprinted polymer exhibits. Therefore, it is suggested that MAA is a superior functional polymer to TFMAA with respect to the atrazine selectivity. It is also found that the polymer in which six equivalents of MAA are used with respect to atrazine is particularly excellent.

Example 3

Figure 8:
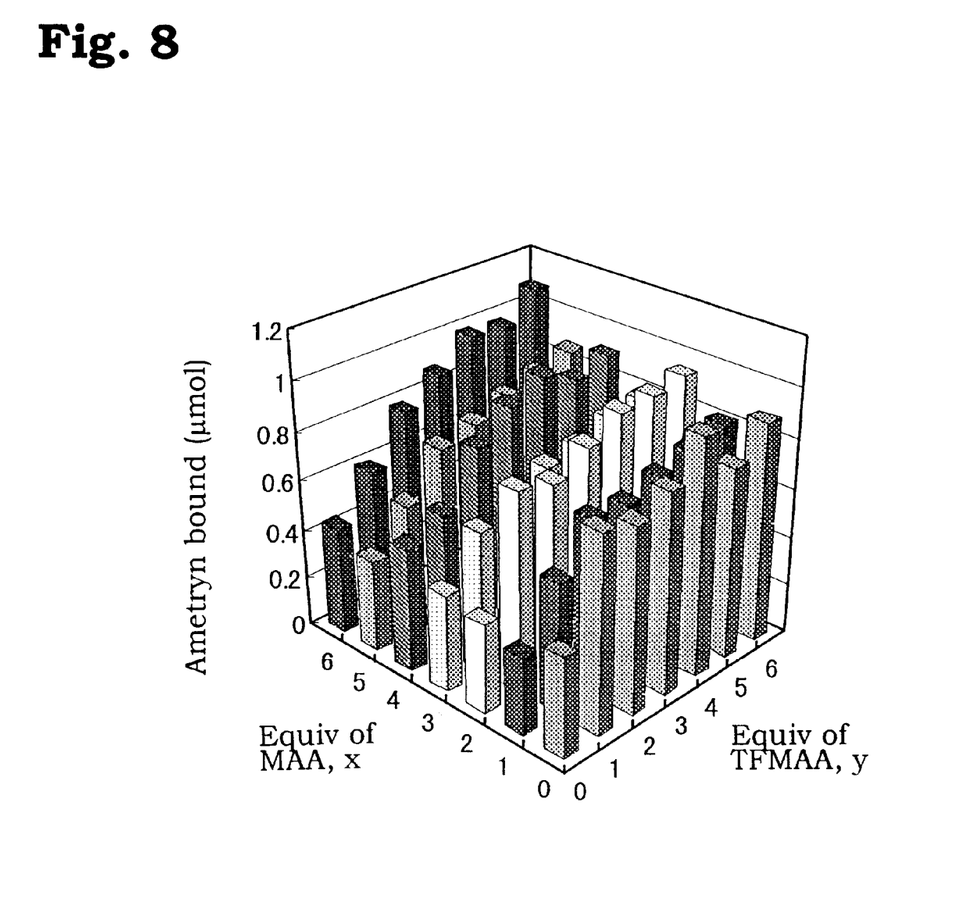
FIG. 8 represents the amounts of ametryn bound to ametryn-imprinted polymers in an ametryn-imprinted polymer library (PL(Ame)) in accordance with the present invention.

A polymer library (PL(Ame)) was synthesized as described in Example 1(1), but the obtained polymers were not washed. Then 1.5 ml of acetonitrile was fed into each of the vessels, which was allowed to stand for 24 hours. Supernatants in the vessels were analyzed by the HPLC analysis to determine the concentrations of unassociated ametryn. The amounts of ametryn bound to the polymers in PL(Ame) were calculated from the initial concentration of ametryn (1.95 μmol, used for synthesis of the ametryn-imprinted polymers) and the concentrations of ametryn remaining in the supernatants. The results are shown in FIG. 8. These results are similar to the results of Example 1. Therefore, it is found possible to obtain roughly evaluated results which are reliable even if ametryn is not dissociated completely with the washing liquid as in Example 1.

Example 4

It is judged from the results of Example 1(4) that a polymer synthesized from one equivalent of MAA and 6 equivalents of TFMAA with respect to one equivalent of ametryn is the most suitable artificial receptor for ametryn. On this basis, an imprinted polymer was synthesized from one equivalent of ametryn, one equivalent of MAA and six equivalents of TFMAA in the same manner as described in Example 1(1). The obtained polymer had a strong binding activity with ametryn.

Example 5

It is judged from the results of Example 2(4), that a polymer synthesized from four equivalents of MAA (zero equivalents of TFMAA) with respect to one equivalent of atrazine is the most suitable artificial receptor for atrazine. On this basis, an imprinted polymer was synthesized from one equivalent of atrazine, four equivalents of MAA (zero equivalents of TFMAA) in the same manner as described in Example 2(1). The obtained polymer had a strong binding activity with atrazine.

Example 6

(1) Preparation of Polymer Library (PL(Cin))

Cinchonine (i.e., (9S)-cinchonan-9-ol) and cinchonidine (i.e., (8α,9R)-cinchonan-9-ol) are antimalarial therapeutic drugs.

The same procedure as described in Example 1 (1) was carried out except that cinchonine (manufactured by Nakaraitesuku) was used as the template substrate in order to synthesize a polymer library of 49 cinchonine-imprinted polymers (hereinafter referred to as PL(Cin)).

(2) Binding Test of PL(Cin) and cinchonine

Figure 9:
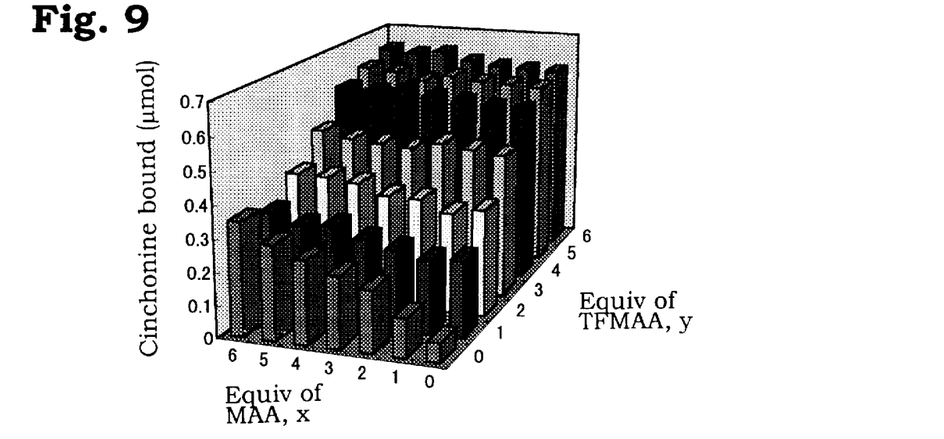
FIG. 9 represents the amounts of cinchonine bound to cinchonine-imprinted polymers in an cinchonine-imprinted polymer library (PL(Cin)) in accordance with the present invention.

The same procedure as described in Example 1(2) was carried out except that 1.5 ml of a 500 $\mu$M cinchonine solution in acetonitrile were fed into each of the vessels where PL(Cin) was produced to calculate the amount of cinchonine bound to each of the polymers of PL(Cin). The results are shown in FIG. 9.

(3) Experiment on the Binding of PL(Cin) to Cinchonidine

Figure 10:
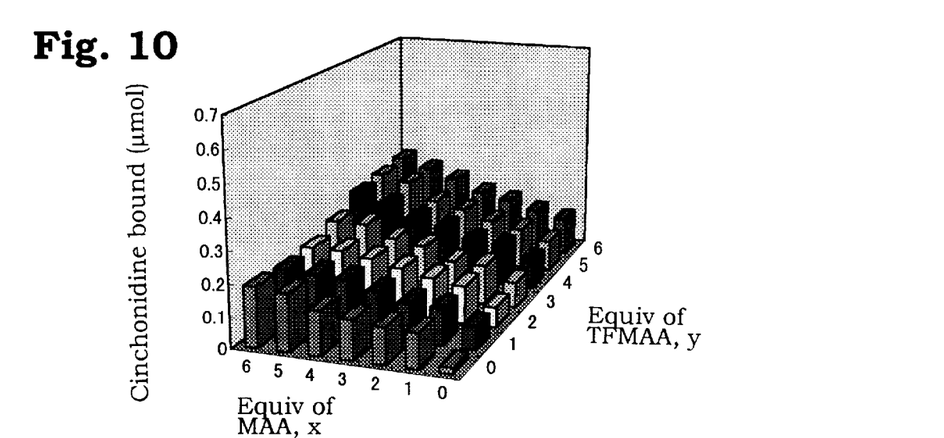
FIG. 10 represents the amounts of cinchonidine bound to the cinchonine-imprinted polymers in the cinchonine-imprinted polymer library (PL(Cin)) in accordance with the present invention.

The same procedure as described in Example 1(3) was carried out except that 1.5 ml of a 50 $\mu$M cinchonidine solution in acetonitrile were fed into the vessels where PL(Cin) was prepared in order to calculate the amount of cinchonidine bound to each of the polymers of PL(Cin). The results are shown in FIG. 10.

In the HPLC analysis of cinchonine and cinchonidine in supernatants, the HPLC system as described in Example 1 was used. In the flow injection analysis, however, an aqueous 10 mM sulfuric acid solution was run at a flow rate of 1.0 ml/min. as a carrier solution, and an excitation wavelength and a fluorescent wavelength of a detector were set to 308 nm and 425 nm, respectively.

(4) Evaluation of PL(Cin) on Selectivity to cinchonine

Figure 11:
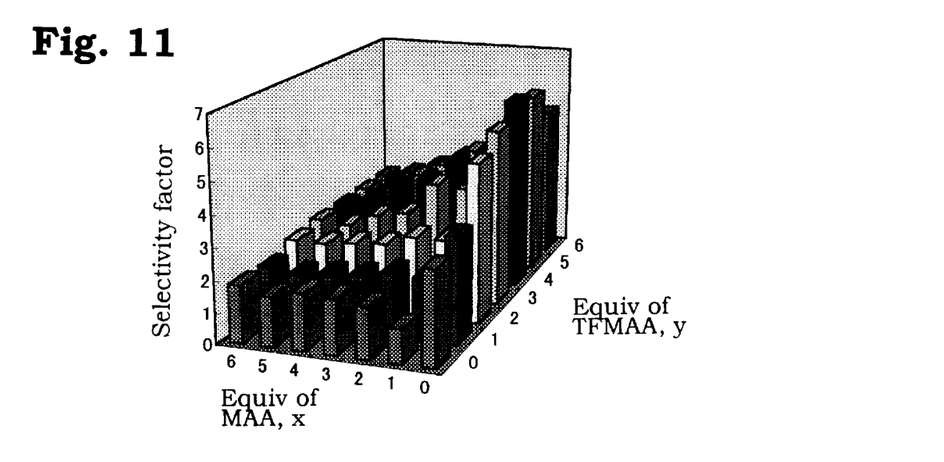
FIG. 11 represents the selectivities of the cinchonine-imprinted polymers to cinchonine in accordance with the present invention.

The ratios of the amounts of cinchonine bound to the cinchonine-imprinted polymers in PL(Cin) to the amounts of cinchonidine bound to the same polymers in PL(Cin) were respectively calculated as the selectivities to cinchonine of the cinchonine-imprinted polymers belonging to PL(Cin). The results are shown in FIG. 11.

FIG. 9 shows that, the amount of cinchonine bound to the cinchonine-imprinted polymer increases when the amount ratio of either of MAA and TFMAA increases with respect to cinchonine. FIG. 10 shows a similar tendency to the tendency shown in FIG. 9, with regard to cinchonidine, but the amount of cinchonidine bound to the cinchonine-imprinted polymers is far smaller than the amount of cinchonine bound to the polymers. It is found from FIG. 11 that the larger the amount ratio of TFMAA to cinchonine in the polymers, the more the selectivity to cinchonine of the polymers improves. Therefore, it is suggested that TFMAA is a superior functional polymer to MAA with respect to the cinchonine selectivity. It is also found that the polymer in which four equivalents of TFMAA are used with respect to cinchonine is particularly excellent.

(5) Quantitation of cinchonine Using PL(cin)

In light of the results of Example 6(4), polymers were prepared in wells of a microplate as in Example 6(1) using 4 equivalents of TFMAA (0 equivalents of MAA) with respect to one equivalent of cinchonine. At this time, 11 wells were used and the prepared polymers were all the same. The resulting polymers were dried, and then cinchonine solutions in concentrations of 0, 10, 20, 30, 40, 50, 60, 80, 100, 200 and 300 mM (1.5 ml each) were fed into the wells. The wells were allowed to stand at room temperature for 24 hours. Then, supernatants in the wells were discharged by suction and the polymers in the wells were dried. The intensity of fluorescence was determined about the polymers in the wells by a fluorescence plate reader (LS-50B manufactured by Perkin Elmer). For determination, the excitation wavelength and fluorescence wavelength were set to 308 nm and 425 nm, respectively.

Figure 12:
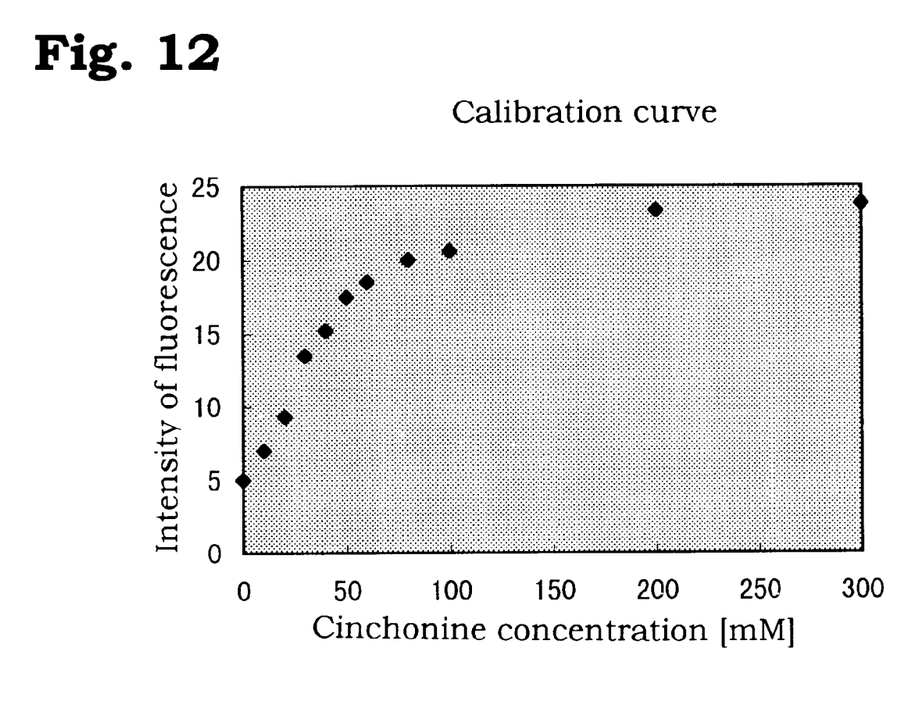
FIG. 12 represents a calibration curve with the concentration of a cinchonine solution and an intensity of fluorescence plotted in abscissa and in ordinate, respectively in accordance with the present invention.

FIG. 12 represents a calibration curve with the concentration of the cinchonine solution and the determined intensity of fluorescence plotted in abscissa and in ordinate, respectively.

The cinchonine concentration of a solution containing cinchonine can be obtained by feeding the solution in a well containing the above-mentioned artificial receptor to associate cinchonine with the artificial receptor, determining the intensity of fluorescence of the resulting artificial receptor and obtaining the concentration of cinchonine using the calibration curve of cinchonine with reference to the determined intensity of fluorescence.

The present invention has realized effective evaluation of molecularly imprinted polymers prepared by use of the in situ method. Further, the present invention has realized simultaneous synthesis and evaluation of a variety of molecularly imprinted polymers by use of the combinatorial chemistry technique. In other words, the invention enables easy and convenient study on conditions such as the kind of a functional monomer compatible with a template substance, the amount ratio of the functional monomer to the template substance, and the combination ratios of functional monomers if plural kinds of functional monomers are used for designing and synthesizing molecularly imprinted polymers.

What is claimed is:

1. A method for evaluating an artificial receptor, comprising the steps of:

subjecting a functional monomer and a crosslinker in the presence of a first template substance in at least one vessel to polymerization, thereby forming a resultant polymer with the template substance;

dissociating the template substance from the polymer and removing the template substance from the at least one vessel by washing an inside of the at least one vessel, thereby preparing an artificial receptor;

feeding a solution of a second template substance, which may be the same or different than the above first template substance, into the at least one vessel to associate the second template substance with the artificial receptor; and then measuring an amount of the unassociated second template substance remaining in the at least one vessel and evaluating the artificial receptor on affinity and selectivity to the second template substance on the basis of a determination result.

2. A method for evaluating an artificial receptor comprising the steps of:

subjecting a functional monomer and a crosslinker in the presence of a template substance in at least one vessel to polymerization; thereby forming a resultant polymer with the template substance; and then measuring an amount of the unassociated template substance remaining in the at least one vessel and evaluating the artificial receptor on affinity and selectivity to the template substance on the basis of a determination result.

3. The method according to claim 1, wherein one vessel is used.

4. The method according to claim 1, wherein, in the polymerizing step, at least one functional monomer and at least one crosslinker in at least one vessel are used to obtain different polymers, and the subsequent steps are conducted to obtain an optimal artificial receptor.

5. The method according to claim 1, wherein the functional monomer is a vinyl monomer selected from the group consisting of a vinyl carboxylic acid, a vinyl sulfonic acid and a vinyl heteroaromatic base.

6. The method according to claim 1, wherein the template substance is selected from the group consisting of a drug, a pesticide a protein an amino acid, a carbohydrate, a coenzyme and a nucleotide base.

7. The method according to claim 1, wherein the template substance is ametryn, atrazine or cinchonine.

8. An artificial receptor as obtained by any one of claims 1 to 7.

9. A method for quantitating a template substance, comprising the steps of:

subjecting a functional monomer and a crosslinker in the presence of a first template substance in at least one vessel to polymerization, thereby forming a resultant polymer with the template substance;

dissociating the template substance from the polymer and removing the template substance from the at least one vessel by washing an inside of the at least one vessel, thereby preparing an artificial receptor;

feeding a sample of a second template substance, which may be same or different than the above first template substance, in an unknown concentration into the vessel to associate the template substance with the artificial receptor, separating the associated product; and measuring an optical parameter of the template substance in the artificial receptor.

10. The method of claim 1, wherein the resultant polymer with the template substance are in the form of a thin film inside of the at least one vessel.

11. The method of claim 2, wherein the resultant polymer with the template substance are in the form of a thin film inside of the at least one vessel.

12. The method of claim 9, wherein the resultant polymer with the template substance are form of a thin film inside of the at least one vessel.

13. The method according to claim 5, wherein the vinyl carboxylic acid is selected from the group consisting of an acrylic acid, methacrylic acid, itaconic acid, trifluoromethacrylic acid, 2-(trifluoromethyl) acrylic acid, vinylbenzoic acid and 4-vinylbenzyliminodiacetic acid; the vinyl sulfonic acid is selected from the group consisting of 2-acrylamido-2-methyl-1-propane sulfonic acid; or the vinyl heteroaromatic base is selected from the group consisting of vinylpyridine, vinylimidazole and 2, 6-bisacrylamidopyridine.

14. The method according to claim 6, wherein the drug is selected from the group consisting of a cinchonine, cinchonidine, theophylline, diazepam, morphine and ephedrine, the hormone is selected from the group consisting of cortisol and enkephalin, the pesticide is selected from the group consisting of atrazine and ametryn, the protein is selected from the group consisting of Rnase A and Urease, the amino acid is selected from the group consisting of phenylalanine, tryptophan, tyrosine and aspartic acid, the carbohydrate is selected from the group consisting of galactose, glucose and fucose, the co-enzyme is pyridoxal or the nucleotide base is adenine.

15. The method according to claim 1, wherein the crosslinker is selected from the group consisting of ethylene glycol, ethylene glycol dimethyl acrylate, 1,4-divinylbenzene, N,N'-methylene-bisacrylamide, N,N'-phenylene-bisacrylamide, ethylene glycol dimethacrylate, trimethylolpropane trimethacrylate, pentaerythritol triacrylate, pentaerythritol tetraacrylate and trimethylpropane trimethacrylate.

16. The method according to claim 1, wherein the functional monomer is present an amount of 1–100 moles with respect to 1 mole of the template substance used.

17. The method according to claim 1, wherein the washing occurs with a washing liquid which is selected from the group consisting of an aliphatic alcohol, water, an acid, a base and a mixture thereof.

18. The method according to claim 9, wherein the optical parameter which is measured is absorbance, intensity of fluorescence or oxygen activity.

* * * * *